United States Patent [19]

Iwataki et al.

[11] 4,249,937
[45] Feb. 10, 1981

[54] CYCLOHEXANE DERIVATIVES

[75] Inventors: Isao Iwataki; Masami Shibuya; Hisao Ishikawa, all of Odawara; Takashi Kawana, Ohiso, all of Japan

[73] Assignee: Nippon Soda Company, Ltd., Tokyo, Japan

[21] Appl. No.: 898,110

[22] Filed: Apr. 20, 1978

[30] Foreign Application Priority Data

| May 23, 1977 | [JP] | Japan | 52-58738 |
| Sep. 20, 1977 | [JP] | Japan | 52-112945 |
| Nov. 16, 1977 | [JP] | Japan | 52-136765 |
| Feb. 28, 1978 | [JP] | Japan | 53-22406 |

[51] Int. Cl.³ .............................................. E05B 65/08
[52] U.S. Cl. ................................ 71/97; 564/300; 71/98; 71/103; 260/438.1; 260/439 R
[58] Field of Search ............ 260/563 R, 438.1, 439 R; 71/98, 103, 97

[56] References Cited

U.S. PATENT DOCUMENTS

| 3,914,316 | 10/1975 | Dunbar et al. | 71/98 X |
| 3,941,826 | 3/1976 | Martin | 71/98 X |
| 3,943,176 | 3/1976 | Dunbar et al. | 71/98 X |
| 4,045,209 | 8/1977 | Hainawtt et al. | 71/98 |

Primary Examiner—Paul F. Shaver
Attorney, Agent, or Firm—George B. Oujevolk

[57] ABSTRACT

Compounds of the general formula

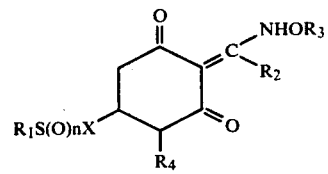

wherein
- $R_1$ is lower alkyl, phenyl, substituted phenyl or benzyl,
- $R_2$ is lower alkyl,
- $R_3$ is lower alkyl or lower alkenyl,
- $R_4$ is hydrogen or lower alkoxycarbonyl,
- X is straight or branched chain lower alkylene, and
- n is 0, 1 or 2;

and metal salts and ammonium salts of the compounds defined hereinabove.

The compounds are useful as herbicides.

25 Claims, No Drawings

CYCLOHEXANE DERIVATIVES

DETAILED DESCRIPTION OF THE INVENTION

The present invention relates to substituted cyclohexane-1,3-dione derivatives, to a process for the preparation thereof and their uses as selective herbicides.

In particular, this invention relates to herbicidally active compositions and to methods of killing undesired plants.

According to the present invention, there is provided a compound of the formula

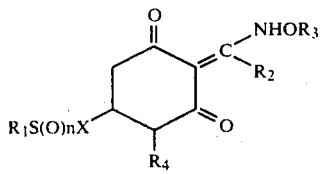

wherein
- $R_1$ is lower alkyl, phenyl, substituted phenyl with halogen, lower alkyl or lower alkoxy, or benzyl,
- $R_2$ is lower alkyl,
- $R_3$ is lower alkyl or lower alkenyl,
- $R_4$ is hydrogen or lower alkoxycarbonyl,
- X is straight or branched chain lower alkylene, and
- n is 0, 1 or 2;

or a metal salt or an ammonium salt of the compound defined hereinabove.

It is disclosed in U.S. Pat. Nos. 3,950,420 and 4,011,256 that some cyclohexane-1,3-dione derivatives are useful as herbicides. Those known cyclohexane-1,3-dione derivatives have alkyl group etc. at the 5-position instead of $R_1S(O)nX-$ of this invention. For example, 2-[1-(allyloxyamino)butylidene]-5,5-dimethylcyclohexane-1,3-dione, 2-[1-(allyloxyamino)butylidene]-4-methoxycarbonyl-5,5-dimethylcyclohexane-1,3-dione, and the like are disclosed.

The inventors have found that the cyclohexane derivatives of the Formula [I] and the salts thereof have superior herbicidal activity to the known cyclohexane-1,3-dione derivatives. The compounds of this invention may be particularly effective in the control of grass weeds, such as barnyard grass (*Echinochloa crus-galli*), blackgrass (*Alopecurus myosuroides*), crabgrass (*Digitaria sanguinalis*), wild oat (*Avena fatua*) and Johnsongrass (*Sorghum halepense*), and they may hardly injure broad leaf crops such as beans, peas, radish, beets and cucumber which easily suffer pyto-toxicity. The compounds of this invention show sufficient herbicidal activity in an amount of one half or one third in comparison with the above-mentioned known cyclohexane-1,3-dione derivatives.

Preferably in the Formula [I], $R_1$ is selected from lower alkyl of 1 to 3 carbon atoms, phenyl and substituted phenyl with chlorine, methyl or methoxy, $R_2$ is selected from lower alkyl of 2 to 3 carbon atoms, $R_3$ is selected from ethyl and allyl, $R_4$ is hydrogen, and X is selected from straight or branched chain lower alkylene of 1 to 3 carbon atoms.

Adding to the herbicidal activity, the compounds of this invention have acaricidal activity.

The compounds of this invention can be prepared in accordance with the following equation:

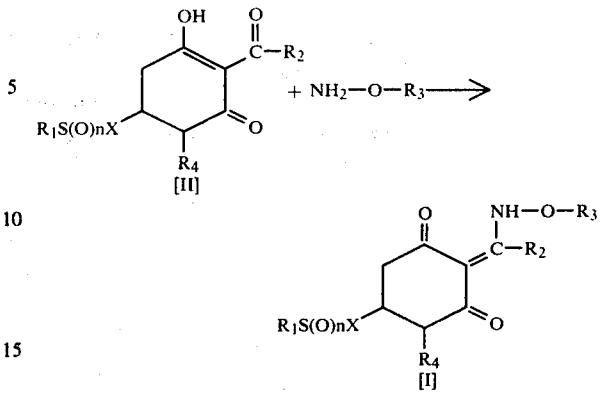

wherein $R_1$, $R_2$, $R_3$, $R_4$, X and n are as previously defined.

The above reaction can be conducted in an inert solvent.

As an inert solvent, acetone, diethyl ether, methyl alcohol, ethyl alcohol, isopropyl alcohol, benzene, tetrahydrofuran, chloroform, acetonitrile, dichloroethane, dichloromethane, ethyl acetate, dioxane, toluene, xylene and dimethyl sulfoxide may be used.

The reaction temperature may be from $-10°$ C. to the boiling point of the reaction solution, preferably from 10° to 60° C., and the reaction may be carried out for several hours or longer.

After the reaction has been completed, the solvent is, if necessary removed, and the reaction mixture is then extracted with an alkaline solution, or is poured into ice-cold water. The alkaline extract or the mixture with water is acidified with hydrochloric acid, and the crude product is isolated from the acidified mixture by extraction with solvent or by filtration.

If the product is crystalline, the crude product can be purified by recrystallization, and if the product is an oily substance, the crude product can be purified by distillation or isolation by column chromatography.

A chemical formula for the resulting purified compound can be assigned by means of an elemental analysis, NMR spectrum and IR spectrum.

The sodium and potassium salts may be prepared by treating a compound of Formula [I] above with sodium or potassium hydroxide in aqueous solution or in an organic solvent such as acetone, methanol, ethanol or dimethylformamide. The salts may be isolated by filtration or by evaporation of the resulting solution.

The calcium, barium, manganese, copper, zinc, nickel, cobalt, iron and silver salts may be prepared from the sodium salt by treatment with the appropriate inorganic metal salt, e.g. calcium chloride, barium chloride, copper sulfate, zinc chloride, nickel chloride, and cobalt nitrate.

The calcium salt may also be prepared by treating a compound of Formula [I] with calcium hydroxide.

Some metal salts of the present invention produced by above-mentioned process may undergo a chemical change or decomposition at a high temperature, and therefore not show a clear melting point. By applying infrared adsorption spectroscopy to the starting material and the reaction product, the formation of the metal salt is evidenced by transference of absorption bands and a change of absorption intensity. Thus, the starting material having the Formula [I] has the absorption due to the carbonyl group at wavelengths 1605 cm$^{-1}$ and 1655 cm$^{-1}$, whereas the corresponding metal salt shows the absorptions at longer wavelengths.

Further, an anion such as OH may be simultaneously coordinated with a metal atom of some metal salts mentioned above.

The structure of the metal salt may be shown as follows:

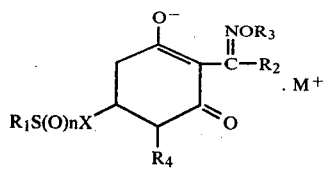

wherein M$^+$ is metal ion such as Na$^+$, 1/2Cathu$^{++}$ or 1/2Cu$^{++}$.

Ammonium salts of this invention may be shown as same as the metal salts, namely,

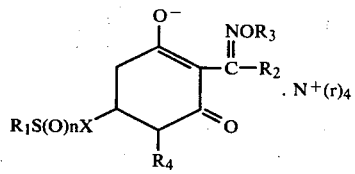

wherein N$^+$(r)$_4$ is quaternary ammonium ion and r is same or different substituent selected from alkyl and benzyl. The ammonium salt can be prepared by the reaction of the compound of the Formula [I] with ammonium hydroxide, N(r)$_4$OH, in the same manner as in the preparation of sodium salt.

It is expected that the compounds represented by the Formula [I] exist in the following four tautomeric forms:

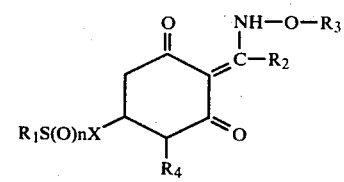

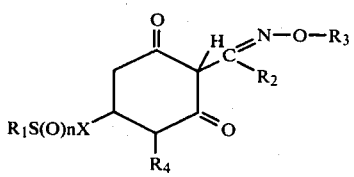

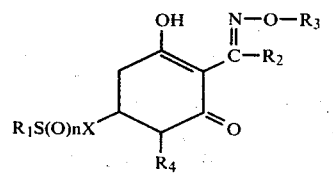

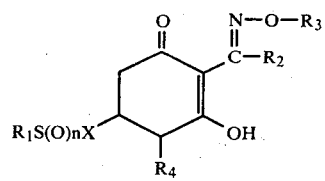

It is similarly expected that the compounds represented by the Formula [II] exist in the following three tautomeric forms:

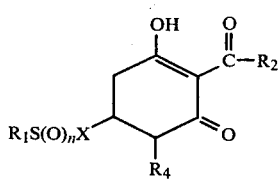

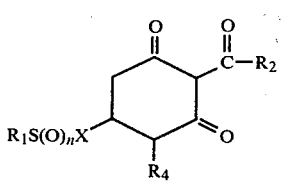

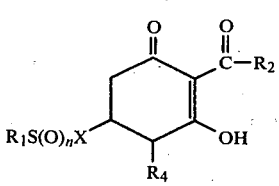

The starting material of the Formula [II] can be prepared in accordance with the following equation wherein R' is lower alkyl:

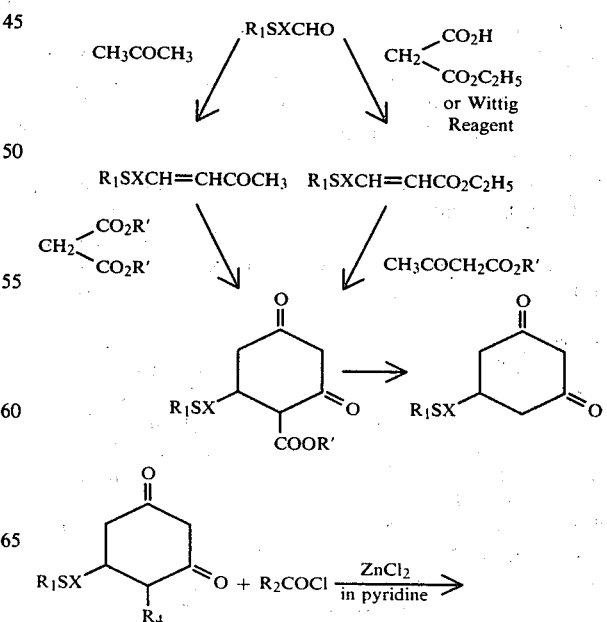

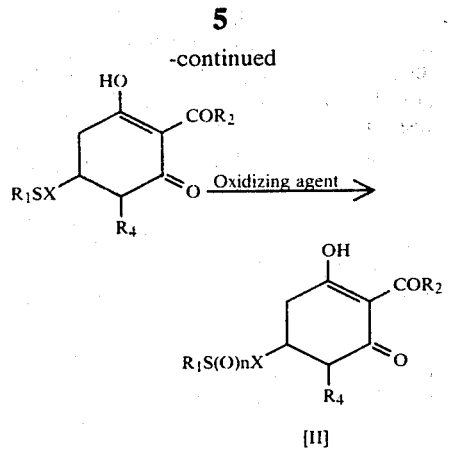

The following Examples illustrate production of compounds according to the invention:

EXAMPLE 1

2-(1-ethoxyaminobutylidene)-5-(2-ethylthiopropyl)-cyclohexane-1,3-dione (Compound No. 1)

5.7 g of 2-butyryl-5-(2-ethylthiopropyl)-cyclohexane-1,3-dione was dissolved in 20 ml of ethanol, 1.4 g of ethoxyamine was added thereto, and the resulting solution was stirred at room temperature for 5 hours. After pouring the reaction solution into ice-cold water and acidifing the mixture with hydrochloric acid, the mixture was extracted with chloroform. The chloroform solution was washed with water, dried over anhydrous magnesium sulfate, and the removal of chloroform by distillation under reduced pressure gave 4.5 g of the desired product as colorless oily material. $n_D^{27.5} 1.5229$

EXAMPLE 2

2-(1-allyloxyaminobutylidene)-5-(2-ethylsulfinylpropyl)-cyclohexane-1,3-dione (Compound No. 2)

6 g of 2-butyryl-5-(2-ethylsulfinylpropyl)-cyclohexane-1,3-dione was dissolved in 30 ml of ethanol. To the solution was added 1.6 g of allyloxyamine and the resulting solution was stirred at room temperature for 15 hours. After completion of the reaction, the reaction solution was treated as in Example 1 to obtain 4.8 g of the desired compound as colorless oily material. $n_D^{27.5} 1.5343$

EXAMPLE 3

2-(1-allyloxyaminobutylidene)-5-(2-methylthioethyl)-cyclohexane-1,3-dione (Compound No. 18)

2.6 g of 2-butyryl-5-(2-methylthioethyl)-cyclohexane-1,3-dione was allowed to react with 0.8 g of allyloxyamine at room temperature for 10 hours in 20 ml of ethanol. After completion of the reaction, the resulting reaction solution was treated as in Example 1 to obtain 3 g of the desired compound as colorless oily material. $n_D^{27} 1.5402$

EXAMPLE 4

2-(1-ethoxyaminopropylidene)-5-[2-(4-chlorophenylthio)ethyl]-cyclohexane-1,3-dione (Compound No. 69)

1.6 g of 2-propionyl-5-[2-(4-chlorophenylthio)ethyl]-cyclohexane-1,3-dione was allowed to react with 0.8 g of ethoxyamine at room temperature for 16 hours in 60 ml of methanol. After completion of the reaction, the resulting reaction solution was treated as in Example 1 to obtain oily product. Purification of the oily product by column chromatography gave 1 g of the desired compound as colorless oily material.
m.p. 42°–43° C.

EXAMPLE 5

2-(1-ethoxyaminopropylidene)-5-[1-(p-tolylthio)isopropyl]cyclohexane-1,3-dione (Compound No. 75)

1.3 g of 2-propionyl-5-[1-(p-tolylthio)isopropyl]cyclohexane-1,3-dione was allowed to react with 0.3 g of allyloxyamine at room temperature for 15 hours in the mixture of 10 ml of benzene and 3 ml of ethanol. After completion of the reaction, the resulting reaction solution was treated as in Example 1 to obtain 1 g of the desired compound.
m.p. 77.5°–79° C.

EXAMPLE 6

Sodium salt of 2-(1-ethoxyaminopropylidene)-5-[2-(4-chlorophenylthio)ethyl]cyclohexane-1,3-dione (Compound No. 93)

0.63 g of sodium methylate was dissolved in 50 ml of methanol and 4.5 g of 2-(1-ethoxyaminopropylidene)-5-[2-(4-chlorophenylthio)ethyl]cyclohexane-1,3-dione obtained in Example 4 was added thereto. Removal of ethanol from the mixture by distillation under reduced pressure gave 4.7 g of light yellow crystals of the desired compound. m.p. 128°–130° C. (dec.)

EXAMPLE 7

Copper salt of 2-(1-ethoxyaminopropylidene)-5-[2-(4-chlorophenylthio)ethyl]cyclohexane-1,3-dione (Compound No. 95)

1.6 g of sodium salt obtained in Example 6 was dissolved in 30 ml of water and 10 ml of aqueous solution of 0.5 g of copper sulfate $CuSO_4.5H_2O$ was added dropwise thereto. After stirring the mixture at room temperature for 30 minutes, precipitated crystals were separated by filtration and recrystallized from the mixed solvent of acetone and water to obtain 1 g of green powder of the desired compound.
m.p. 122° C. (dec.)

EXAMPLE 8

Tetrabutylammonium salt monohydrate of 2-(1-ethoxyaminopropylidene)-5-[2-(4-chlorophenylthio)ethyl]cyclohexane-1,3-dione (Compound No. 96)

1.5 g of 2-(1-ethoxyaminopropylidene)-5-[2-(4-chlorophenylthio)-ethyl]cyclohexane-1,3-dione obtained as in Example 4 was dissolved in 15 ml of methanol. To the solution was added 10 g of 10% methanol solution of tetrabutylammonium hydroxide, and then the methanol was removed by distillation under reduced pressure. The residual oily product was dissolved in 50 ml of water, decolorized by active carbon, and extracted with 50 ml of dichloromethane. After drying the dichloromethane solution over anhydrous magnesium sulfate, dichloromethane was distilled off under reduced pressure. The residual oily material was allowed to stand to obtain crystals, which was recrystallized from benzene-ligroin to yield 1.6 g of white crystal of the desired compound.
m.p. 80°–82° C.

EXAMPLE 9

2-(1-allyloxyaminobutylidene)-5-(2-methylsulfonylethyl)-4-methoxycarbonylcyclohexane-1,3-dione (Compound No. 100)

3.5 g of 2-butyryl-5-(2-methylsulfonylethyl)-4-methoxycarbonyl-cyclohexane-1,3-dione was allowed to react with 0.9 g of allyloxyamine at room temperature for 5 hours in 20 ml of ethanol. After completion of the reaction, the resulting reaction solution was treated as in Example 1 to obtain 3.1 g of white crystal of the desired compound. m.p. 96.5° C.

In addition to the above-mentioned compounds, some typical compounds of this invention are listed in Table 1:

TABLE 1.

$$R_1S(O)_nX\underset{R_4}{\overset{O}{\bigcirc}}\overset{NHOR_3}{\underset{O}{=C}}_{R_2}$$

| Compound No. | $R_1S(O)_nX-$ | $R_2$ | $R_3$ | $R_4$ | Salt | Physical Constant [m.p.] °C. |
|---|---|---|---|---|---|---|
| 1 | $C_2H_5SCHCH_2-$<br>$\quad\|\quad$<br>$\quad CH_3$ | $C_3H_7{}^n$ | $C_2H_5$ | H | — | $n_D{}^{27.5}$ 1.5229 |
| 2 | $\overset{O}{\underset{\uparrow}{}}$<br>$C_2H_5SCHCH_2-$<br>$\quad\|\quad$<br>$\quad CH_3$ | " | $CH_2CH=CH_2$ | " | — | $n_D{}^{27.5}$ 1.5343 |
| 3 | $C_2H_5SO_2CHCH_2-$<br>$\quad\|\quad$<br>$\quad CH_3$ | " | " | " | — | $n_D{}^{30}$ 1.5266 |
| 4 | $CH_3SO_2CHCH_2-$<br>$\quad\|\quad$<br>$\quad CH_3$ | " | " | " | — | [80–82] |
| 5 | $nC_4H_9SO_2CHCH_2-$<br>$\quad\|\quad$<br>$\quad CH_3$ | " | " | " | — | $n_D{}^{30}$ 1.5232 |
| 6 | $C_2H_5SCH_2CH-$<br>$\quad\quad\quad\|\quad$<br>$\quad\quad\quad CH_3$ | " | " | " | — | $n_D{}^{29}$ 1.5291 |
| 7 | $C_2H_5SCH-$<br>$\quad\|\quad$<br>$\quad C_2H_5$ | " | " | " | — | $n_D{}^{30}$ 1.5337 |
| 8 | $nC_4H_9SCHCH_2-$<br>$\quad\|\quad$<br>$\quad CH_3$ | " | $C_2H_5$ | " | — | $n_D{}^{30}$ 1.5135 |
| 9 | $nC_3H_7SCHCH_2-$<br>$\quad\|\quad$<br>$\quad CH_3$ | " | $CH_2CH=CH_2$ | " | — | $n_D{}^{30}$ 1.5280 |
| 10 | $nC_3H_7SO_2CHCH_2-$<br>$\quad\|\quad$<br>$\quad CH_3$ | " | $C_2H_5$ | " | — | $n_D{}^{30}$ 1.5205 |
| 11 | $CH_3SCHCH_2-$<br>$\quad\|\quad$<br>$\quad CH_3$ | " | $CH_2CH=CH_2$ | " | — | $n_D{}^{30}$ 1.5352 |
| 12 | $CH_3SCH-$<br>$\quad\|\quad$<br>$\quad CH_3$ | " | " | " | — | $n_D{}^{29}$ 1.5397 |
| 13 | $C_2H_5SCH_2-$ | " | " | " | — | $n_D{}^{30}$ 1.5376 |
| 14 | $C_2H_5SO_2CH_2-$ | " | " | " | — | [62–64] |
| 15 | ⟨Ph⟩—$SC_2H_4-$ | " | " | " | — | $n_D{}^{30}$ 1.5738 |
| 16 | ⟨Ph⟩—$SO_2C_2H_4-$ | " | " | " | — | [57–58] |
| 17 | $CH_3SCHCH_2-$<br>$\quad\|\quad$<br>$\quad CH_3$ | " | " | " | Na | — |
| 18 | $CH_3SC_2H_4-$ | " | " | " | — | $n_D{}^{27}$ 1.5402 |
| 19 | $C_2H_5SC_2H_4-$ | " | " | " | — | $n_D{}^{20}$ 1.5380 |
| 20 | " | " | $C_2H_5$ | " | — | $n_D{}^{20}$ 1.5322 |
| 21 | $\overset{O}{\underset{\uparrow}{}}$<br>$C_2H_5SC_2H_4-$ | " | $CH_2CH=CH_2$ | " | — | [37–40] |
| 22 | $C_2H_5SO_2C_2H_4-$ | " | " | " | — | [52–54] |
| 23 | $C_2H_5SC_2H_4-$ | $C_2H_5$ | " | " | — | $n_D{}^{26}$ 1.5400 |

TABLE 1.-continued $$\text{R}_1\text{S(O)}_n\text{X} - \underset{\underset{\text{R}_4}{\parallel}}{\overset{\overset{\text{O}}{\parallel}}{\bigcirc}} = \text{C} \overset{\text{NHOR}_3}{\underset{\text{R}_2}{}}$$

| Compound No. | $R_1S(O)_nX-$ | $R_2$ | $R_3$ | $R_4$ | Salt | Physical Constant [m.p.] °C. |
|---|---|---|---|---|---|---|
| 24 | $C_2H_5SC_2H_4-$ ↑O | $C_3H_7{}^n$ | $C_2H_5$ | " | — | $n_D^{26}$ 1.5329 |
| 25 | $CH_3SO_2C_2H_4-$ | " | $CH_2CH=CH_2$ | " | — | [54-56] |
| 26 | $C_2H_5SC_2H_4-$ ↑O | " | $C_2H_5$ | " | Ca | [85-90] |
| 27 | $iC_3H_7SC_2H_4-$ | " | $CH_2CH=CH_2$ | " | — | $n_D^{25}$ 1.5310 |
| 28 | " | " | $C_2H_5$ | " | — | $n_D^{27}$ 1.5259 |
| 29 | $iC_3H_7SC_2H_4-$ ↑O | " | $CH_2CH=CH_2$ | " | — | $n_D^{27}$ 1.5340 |
| 30 | $iC_3H_7SO_2C_2H_4-$ | " | " | " | — | [76-78] |
| 31 | $CH_3SC_2H_4-$ | " | $C_2H_5$ | " | — | $n_D^{27}$ 1.5339 |
| 32 | " | $C_2H_5$ | $CH_2CH=CH_2$ | " | — | $n_D^{27}$ 1.5488 |
| 33 | " | " | $C_2H_5$ | " | — | $n_D^{27}$ 1.5414 |
| 34 | $C_2H_5SO_2C_2H_4-$ | $C_3H_7{}^n$ | " | " | — | [84-85] |
| 35 | $CH_3SC_2H_4-$ ↑O | " | $CH_2CH=CH_2$ | " | — | $n_D^{25}$ 1.5420 |
| 36 | $nC_3H_7SC_2H_4-$ | " | " | " | — | $n_D^{25}$ 1.5305 |
| 37 | " | " | $C_2H_5$ | " | — | $n_D^{25}$ 1.5260 |
| 38 | $nC_3H_7SC_2H_4-$ ↑O | " | $CH_2CH=CH_2$ | " | — | $n_D^{23}$ 1.5350 |
| 39 | $nC_3H_7SO_2C_2H_4-$ | " | " | " | — | [70-72] |
| 40 | $CH_3SO_2C_2H_4-$ | " | " | " | Na | [198-199]dec. |
| 41 | " | " | $C_2H_5$ | " | — | [87-88] |
| 42 | $CH_3SC_2H_4-$ | $CH_3$ | $CH_2CH=CH_2$ | " | — | $n_D^{30}$ 1.5513 |
| 43 | $CH_3SO_2C_2H_4-$ | " | " | " | — | [84-85] |
| 44 | $C_6H_5-SC_2H_4-$ | $C_2H_5$ | " | " | — | $n_D^{30}$ 1.5813 |
| 45 | $CH_3SO_2C_2H_4-$ | " | $C_2H_5$ | " | — | [136-138] |
| 46 | $C_2H_5SCHCH_2-$<br>\|<br>$CH_3$ | " | $CH_2CH=CH_2$ | " | — | $n_D^{30.5}$ 1.5347 |
| 47 | " | " | " | " | Na |  |
| 48 | $CH_3SC-$<br>(with $CH_3$, $CH_3$) | $C_3H_7{}^n$ | " | " | — | $n_D^{22.5}$ 1.5424 |
| 49 | $C_2H_5SC-$<br>(with $CH_3$, $CH_3$) | " | " | " | — | $n_D^{24.5}$ 1.5380 |
| 50 | $C_2H_5SCHCH_2-$<br>\|<br>$CH_3$ | " | " | " | — | $n_D^{33}$ 1.5305 |
| 51 | $C_6H_5-SCH_2-$ | " | " | " | — | $n_D^{31}$ 1.5794 |
| 52 | $C_2H_5SC-$<br>(with $CH_3$, $CH_3$) | $C_2H_5$ | " | " | — | $n_D^{24.5}$ 1.5452 |
| 53 | $CH_3SC-$<br>(with $CH_3$, $CH_3$) | " | " | " | — | $n_D^{25.2}$ 1.5478 |
| 54 | $C_6H_5-SC_2H_4-$ | $C_3H_7{}^n$ | $C_2H_5$ | " | — | $n_D^{24}$ 1.5700 |
| 55 | $C_6H_5-SO_2C_2H_4-$ | $C_2H_5$ | $CH_2CH=CH_2$ | " | — | $n_D^{23}$ 1.5659 |

TABLE 1.-continued $$R_1S(O)_nX\text{—cyclohexane-1,3-dione with }=C(R_2)\text{—NHOR}_3\text{ and }R_4$$

| Compound No. | $R_1S(O)_nX-$ | $R_2$ | $R_3$ | $R_4$ | Salt | Physical Constant [m.p.] °C. |
|---|---|---|---|---|---|---|
| 56 | CH₃SCH(CH₃)CH₂— | $C_3H_7{}^n$ | $C_2H_5$ | " | — | $n_D^{23}$ 1.5313 |
| 57 | nC₃H₇SC₂H₄— | $C_2H_5$ | " | " | — | $n_D^{21}$ 1.5339 |
| 58 | C₆H₅SCH₂— | " | " | " | — | $n_D^{25}$ 1.5820 |
| 59 | iC₃H₇SCH₂— | $C_3H_7{}^n$ | CH₂CH=CH₂ | " | — | $n_D^{20}$ 1.5336 |
| 60 | (CH₃)₂(CH₃S)C— | " | $C_2H_5$ | " | — | $n_D^{27}$ 1.5355 |
| 61 | " | $C_2H_5$ | " | " | — | $n_D^{27}$ 1.5415 |
| 62 | CH₃SCH(CH₃)CH₂— | " | " | " | — | $n_D^{28}$ 1.5365 |
| 63 | C₂H₅SCH(CH₃)CH₂— | $C_3H_7{}^n$ | " | " | Na | [133–134]dec. |
| 64 | " | " | " | " | Cu | [137–138]dec. |
| 65 | " | " | " | " | Ca | [181–182]dec. |
| 66 | " | " | " | " | Ni | [175–176]dec. |
| 67 | " | " | " | " | Fe | [137–138]dec. |
| 68 | 4-Cl-C₆H₄-SCH₂CH₂— | " | CH₂CH=CH₂ | " | — | $n_D^{31}$ 1.5828 |
| 69 | " | $C_2H_5$ | $C_2H_5$ | " | — | [42–43] |
| 70 | " | " | CH₂CH=CH₂ | " | — | $n_D^{31}$ 1.5848 |
| 71 | 4-Cl-C₆H₄-SC(CH₃)₂— | " | $C_2H_5$ | " | — | [69–71] |
| 72 | " | " | CH₂CH=CH₂ | " | — | [50–53] |
| 73 | 4-Cl-C₆H₄-S-CH(CH₃)CH₂— | " | " | " | — | $n_D^{25}$ 1.5810 |
| 74 | " | " | $C_2H_5$ | " | — | $n_D^{25}$ 1.5785 |
| 75 | 4-CH₃-C₆H₄-SC(CH₃)₂— | " | " | " | — | [77.5–79] |
| 76 | C₆H₅CH₂SC₂H₄— | $C_3H_7{}^n$ | CH₂CH=CH₂ | " | — | $n_D^{27}$ 1.5700 |
| 77 | " | $C_2H_5$ | " | " | — | $n_D^{27}$ 1.5760 |
| 78 | 4-CH₃-C₆H₄-SC₂H₄— | " | $C_2H_5$ | " | — | $n_D^{22}$ 1.5774 |
| 79 | " | " | CH₂CH=CH₂ | " | — | $n_D^{22}$ 1.5798 |
| 80 | 2-CH₃-C₆H₄-SC₂H₄— | " | " | " | — | $n_D^{22}$ 1.5790 |
| 81 | " | " | $C_2H_5$ | " | — | $n_D^{23}$ 1.5734 |
| 82 | 3-CH₃-C₆H₄-SC₂H₄— | " | CH₂CH=CH₂ | " | — | $n_D^{23}$ 1.5781 |
| 83 | " | " | $C_2H_5$ | " | — | $n_D^{22}$ 1.5722 |
| 84 | 4-CH₃O-C₆H₄-SC₂H₄— | " | " | " | — | $n_D^{23}$ 1.5790 |
| 85 | " | " | CH₂CH=CH₂ | " | — | $n_D^{23}$ 1.5811 |
| 86 | 2,4-Cl₂-C₆H₃-SC₂H₄— | " | $C_2H_5$ | " | — | [69–70] |
| 87 | 4-Cl-C₆H₄-SO₂C₂H₄— | " | " | " | — | [96–97] |

TABLE 1.-continued

Structure:
$$R_1S(O)_nX \text{ (cyclohexane ring with)} =C\begin{smallmatrix}NHOR_3\\R_2\end{smallmatrix}, \text{ O at 1,3-positions, } R_4 \text{ substituent}$$

| Compound No. | $R_1S(O)_nX-$ | $R_2$ | $R_3$ | $R_4$ | Salt | Physical Constant [m.p.] °C |
|---|---|---|---|---|---|---|
| 88 | CH$_3$-(2,4-dimethylphenyl)-SC$_2$H$_4$- | " | CH$_2$CH=CH$_2$ | " | — | $n_D^{18}$ 1.5811 |
| 89 | " | " | C$_2$H$_5$ | " | — | $n_D^{31.5}$ 1.5732 |
| 90 | Cl-(phenyl)-SC$_2$H$_4$- | " | " | " | (phenyl)-CH$_2$N(CH$_3$)$_3^+$ | |
| 91 | " | " | " | " | (phenyl)-CH$_2$-N$^+$(CH$_3$)$_2$-C$_{16}$H$_{33}$ | |
| 92 | Cl-(phenyl)-S(=O)C$_2$H$_4$- | " | " | " | — | [93–95] |
| 93 | Cl-(phenyl)-SC$_2$H$_4$- | " | " | " | Na | [128–130]dec. |
| 94 | " | " | " | " | Ca | [172–173]dec. |
| 95 | " | " | " | " | Cu | [122]dec. |
| 96 | " | " | " | " | N(C$_4$H$_9^n$)$_4^+$ · H$_2$O | [80–82] |
| 97 | " | CH$_3$ | " | " | — | [48–50] |
| 98 | C$_2$H$_5$SC$_2$H$_4$- | C$_3$H$_7^n$ | CH$_2$CH=CH$_2$ | COOC$_2$H$_5$ | — | $n_D^{24}$ 1.5268 |
| 99 | " | " | " | COOCH$_3$ | — | $n_D^{26.5}$ 1.5324 |
| 100 | CH$_3$SO$_2$C$_2$H$_4$- | " | " | " | — | [96.5] |

As mentioned previously, the compounds of this invention possess superior herbicidal activity. The compounds may be applied directly to the soil as pre-emergence treatment or as post-emergence treatment to plant foliage, or they can be mixed intimately with soil. The preferred treatment is after emergence of the plant foliage and the compounds may be applied to soil or to plant foliage in amounts of 10 g or more per 10 are.

A herbicidal composition having a compound of this invention as its active ingredient may be formulated by mixing suitable carriers in a form generally used in agricultural chemicals, such as wettable powder, emulsifiable concentrate, granular formulation, water soluble powder and aerosol. As solid carriers, bentonite, diatomaceous earth, apatite, gypsum, talc, pyrophyllite, vermiculite and clay may be used. As liquid carriers, kerosene, mineral oil, petroleum, solvent naphtha, benzene, xylene, cyclohexane, cyclohexanone, dimethylformamide, alcohol and acetone may be used. A surface active agent may also be added, in order to give a homogeneous and stable formulation.

Compounds of this invention can also be applied admixed with other chemicals, which are used in agronomic and horticultural management and which are compatible with such compounds. Such chemicals can be, but are not restricted to, the classes of chemical commonly known as plant nutrients, fertilizers, insecticides, acaricides, fungicides, herbicides and nematocides.

For admixture of the compound with known herbicides, the use is recommended of triazine derivatives such as simazine, propazine and prometryn, carbamate derivatives such as phenmedipham, urea derivatives such as metabenzthiazuron and linuron, and heterocyclic compounds such as pyrazon and lenacil.

The concentration of the active ingredient in a herbicidal composition of this invention may vary according to type of formulation, and the concentration is, for example, in the range of 5–80 weight percent, preferably 10–60 weight percent, in wettable powder; 5–70 weight percent, preferably 20–60 weight percent, in emulsifiable concentrates; and 0.5–30 weight percent, preferably 1–10 weight percent, in granular formulation.

A wettable powder or an emulsifiable concentrate thus produced may be diluted with water to a specified concentration and used as a liquid suspension or a liquid emulsion for treating soils or plant foliage. Further, a granular formulation may be directly used for soil or foliage treatment.

Non-limiting examples of herbicidal compositions according to the invention are as follows:

EXAMPLE 10

Wettable Powder

| | Parts by weight |
|---|---|
| Compound No. 1 | 30 |
| White carbon | 30 |
| Diatomaceous earth | 32 |
| Sodium alkylsulfate | 8 |

These are mixed homogeneously and reduced to fine particles to provide a wettable powder containing 30% of active ingredient. In use, it is diluted to a desired concentration with water, and is sprayed as a suspension.

EXAMPLE 11

Emulsifiable Concentrate

|  | Parts by weight |
|---|---|
| Compound 25 | 40 |
| Xylene | 35 |
| Dimethylformamide | 15 |
| Polyoxyethylene phenylether | 10 |

These are mixed together to provide an emulsifiable concentrate containing 40% of the active ingredient. In use, it is diluted to a desired concentration with water, and is sprayed as an emulsion.

EXAMPLE 12

Granular Formulation

|  | Parts by weight |
|---|---|
| Compound 69 | 7 |
| Talc | 38 |
| Bentonite | 10 |
| Clay | 38 |
| Sodium alkylsulfate | 7 |

These are mixed homogeneously and reduced to fine particles. The fine particles are made into granules, each having a diameter in the range of 0.5–1.0 mm, to provide a granular formulation containing 7% of the active ingredient. In use it is directly applied.

The herbicidal effects of compounds of this invention are illustrated by the following tests:

TEST 1

Seeds of crabgrass, wild oat, lamb's-quarters and liuid amaranth were planted in each pot having a surface area of 100 cm². When the plants were grown to 2–5 leaves stage, an aqueous suspension, prepared by diluting an emulsifiable concentrate with water to a specified concentration was sprayed on the foliage of the test plants, and the pots were kept in a green-house. Fourteen days after spraying, the degree of damage to the each plant was observed and evaluated on the scale of values of 0–10, which has the following meanings:

0: no effect
10: plant completely destroyed

The compounds had no effect to lamb's-quarters and liuid amaranth, namely, the degree of damage was 0.

The results are shown in Table 2.

TABLE 2

| Compound No. | Application Rate (g/10 are) 50 | | Application Rate (g/10 are) 25 | |
|---|---|---|---|---|
|  | crabgrass | wild oat | crabgrass | wild oat |
| 1 | 10 | 10 | 10 | 10 |
| 2 | 10 | 10 | 8 | 9 |
| 4 | 10 | 10 | 10 | 10 |
| 5 | 10 | 10 | 8 | 9 |
| 6 | 10 | 10 | 9 | 9 |
| 9 | 10 | 10 | 9 | 7 |
| 10 | 9 | 10 | 7 | 9 |
| 11 | 10 | 10 | 10 | 10 |
| 12 | 10 | 10 | 10 | 10 |
| 13 | 10 | 7 | 10 | 3 |
| 15 | 10 | 10 | 10 | 10 |
| 16 | 10 | 10 | 10 | 10 |
| 18 | 10 | 10 | 9 | 9 |
| 19 | 10 | 10 | 10 | 10 |
| 20 | 10 | 10 | 10 | 10 |
| 21 | 10 | 10 | 9 | 5 |
| 22 | 10 | 10 | 10 | 10 |
| 23 | 10 | 10 | 10 | 10 |
| 24 | 10 | 10 | 9 | 9 |
| 25 | 10 | 10 | 10 | 10 |
| 26 | 10 | 10 | 9 | 8 |
| 27 | 10 | 10 | 10 | 10 |
| 28 | 10 | 10 | 10 | 10 |
| 29 | 10 | 10 | 10 | 10 |
| 30 | 10 | 10 | 10 | 10 |
| 31 | 10 | 10 | 8 | 8 |
| 32 | 10 | 10 | 10 | 10 |
| 34 | 10 | 10 | 10 | 10 |
| 35 | 10 | 10 | 10 | 10 |
| 36 | 10 | 10 | 10 | 10 |
| 37 | 10 | 10 | 10 | 10 |
| 38 | 10 | 10 | 10 | 10 |
| 39 | 10 | 10 | 10 | 10 |
| 40 | 10 | 10 | 10 | 10 |
| 43 | 10 | 9 | 8 | 4 |
| 44 | 10 | 10 | 10 | 10 |
| 46 | 10 | 10 | 10 | 10 |
| 47 | 10 | 10 | 10 | 10 |
| 48 | 10 | 10 | 10 | 10 |
| 49 | 10 | 10 | 10 | 10 |
| 50 | 10 | 10 | 10 | 10 |
| 53 | 10 | 10 | 10 | 9 |
| 55 | 10 | 10 | 9 | 5 |
| 56 | 10 | 10 | 10 | 10 |
| 57 | 10 | 10 | 10 | 10 |
| 60 | 10 | 10 | 10 | 10 |
| 61 | 10 | 10 | 10 | 10 |
| 68 | 10 | 10 | 4 | 10 |
| 69 | 10 | 10 | 10 | 10 |
| 70 | 10 | 10 | 10 | 10 |
| 73 | 10 | 10 | 8 | 10 |
| 74 | 10 | 10 | 9 | 10 |
| 77 | 9 | 10 | 5 | 10 |
| 78 | 10 | 10 | 10 | 10 |
| 79 | 10 | 10 | 10 | 10 |
| 80 | 10 | 10 | 9 | 10 |
| 81 | 10 | 10 | 10 | 10 |
| 82 | 10 | 9 | 8 | 4 |
| 83 | 10 | 9 | 9 | 4 |
| 84 | 10 | 10 | 10 | 10 |
| 85 | 10 | 10 | 9 | 10 |
| 86 | 10 | 10 | 9 | 10 |
| 87 | 10 | 10 | 9 | 10 |
| 88 | 10 | 10 | 9 | 10 |
| 89 | 10 | 10 | 10 | 10 |
| 90 | 10 | 10 | 7 | 3 |
| 92 | 10 | 10 | 10 | 10 |
| 93 | 10 | 10 | 10 | 10 |
| 94 | 10 | 10 | 10 | 10 |
| 95 | 10 | 10 | 9 | 10 |
| 96 | 10 | 10 | 10 | 10 |
| 97 | 10 | 10 | 10 | 10 |
| 98 | 10 | 10 | 6 | 9 |
| 99 | 10 | 10 | 8 | 10 |
| Comparative Compound* 1 | 10 | 8 | 4 | 2 |

TABLE 2-continued

| | Application Rate (g/10 are) | | | |
|---|---|---|---|---|
| | 50 | | 25 | |
| Compound No. | crabgrass | wild oat | crabgrass | wild oat |
| 2 | 10 | 9 | 5 | 4 |

*Comparative compound

1. 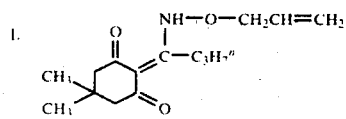

U.S. Pat.No. 3,950,420

2. 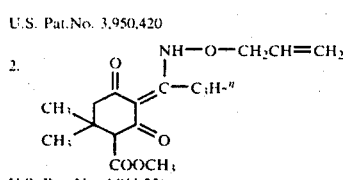

U.S. Pat. No. 4,011,256

We claim:

1. A compound selected from the group consisting of (a) a cyclohexane derivative of the general formula

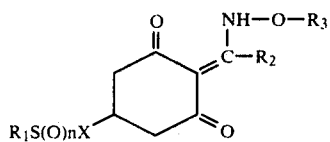

wherein
$R_1$ is selected from the group consisting of lower alkyl, benzyl, phenyl and substituted phenyl with chlorine, methyl or methoxy,
$R_2$ is lower alkyl,
$R_3$ is selected from the group consisting of lower alkyl and lower alkenyl,
X is straight or branched alkylene having 2 or 3 carbon atoms, and
n is 0, 1 or 2, and
(b) a metal salt of the cyclohexane derivative in (a) wherein the metal is selected from the group consisting of sodium, calcium, copper and iron.

2. The compound according to claim 1, wherein $R_1$ is selected from the group consisting of lower alkyl having 1 to 3 carbon atoms, phenyl and substituted phenyl with chlorine methyl or methoxy; $R_2$ is lower alkyl having 1 to 3 carbon atoms; and $R_3$ is ethyl or allyl.

3. The compound according to claim 2, wherein $R_1$ is lower alkyl having 1 to 3 carbon atoms, and $R_2$ is lower alkyl having 2 or 3 carbon atoms.

4. The compound according to claim 2, wherein $R_1$ is phenyl, or substituted phenyl with chlorine or methyl, and $R_2$ is lower alkyl having 2 or 3 carbon atoms.

5. A compound according to claim 3, wherein X is ethylene.

6. A compound according to claim 3, wherein X is branched lower alkylene.

7. A compound according to claim 4, wherein X is ethylene.

8. A compound according to claim 4, wherein X is branched lower alkylene.

9. A herbicidal composition, comprising an inert carrier and an effective amount of a compound of claim 1.

10. A herbicidal composition, comprising an inert carrier and an effective amount of a compound of claim 2.

11. A herbicidal composition, comprising an inert carrier and an effective amount of a compound of claim 3.

12. A herbicidal composition, comprising an inert carrier and an effective amount of a compound of claim 4.

13. A herbicidal composition, comprising an inert carrier and an effective amount of a compound of claim 5.

14. A herbicidal composition, comprising an inert carrier and an effective amount of a compound of claim 6.

15. A herbicidal composition, comprising an inert carrier and an effective amount of a compound of claim 7.

16. A herbicidal composition, comprising an inert carrier and an effective amount of a compound of claim 8.

17. A method for the control of weeds, comprising applying to the locus to be protected an effective amount of a compound of claim 1.

18. A method for the control of weeds, comprising applying to the locus to be protected an effective amount of a compound of claim 2.

19. A method for the control of weeds, comprising applying to the locus to be protected an effective amount of a compound of claim 3.

20. A method for the control of weeds, comprising applying to the locus to be protected an effective amount of a compound of claim 3.

21. A method for the control of weeds, comprising applying to the locus to be protected an effective amount of a compound of claim 5.

22. A method for the control of weeds, comprising applying to the locus to be protected an effective amount of a compound of claim 6.

23. A method for the control of weeds, comprising applying to the locus to be protected an effective amount of a compound of claim 7.

24. A method for the control of weeds, comprising applying to the locus to be protected an effective amount of a compound of claim 8.

25. The compound according to claim 2, wherein $R_2$ is lower alkyl having 2 or 3 carbon atoms, and $R_1S(O)nX-$ is selected from the group consisting of
2-methylthiopropyl,
2-ethylthiopropyl,
2-methylsulfonylethyl,
2-propylthioethyl,
1-methylthioisopropyl,
2-(4-chlorophenylthio)ethyl,
2-(p-tolylthio)ethyl,
2-(4-chlorophenylsulfinyl)ethyl and
2-(4-chlorophenylsulfonyl)ethyl.

* * * * *